US007866817B2

(12) United States Patent
Polat

(10) Patent No.: US 7,866,817 B2
(45) Date of Patent: Jan. 11, 2011

(54) SYSTEMS AND METHODS FOR IMPROVING VISUAL PERCEPTION

(75) Inventor: Uri Polat, Ramat Gan (IL)

(73) Assignee: Ucansi, Inc., New York, NY (US)

( * ) Notice: Subject to any disclaimer, the term of this patent is extended or adjusted under 35 U.S.C. 154(b) by 182 days.

(21) Appl. No.: 11/885,229

(22) PCT Filed: Aug. 31, 2005

(86) PCT No.: PCT/IL2005/000927

§ 371 (c)(1),
(2), (4) Date: Dec. 18, 2008

(87) PCT Pub. No.: WO2006/025056

PCT Pub. Date: Mar. 9, 2006

(65) Prior Publication Data

US 2010/0097571 A1 Apr. 22, 2010

Related U.S. Application Data

(60) Provisional application No. 60/607,081, filed on Sep. 3, 2004.

(51) Int. Cl.
*A61B 3/08* (2006.01)
*A61B 3/00* (2006.01)
*A61B 3/02* (2006.01)

(52) U.S. Cl. ........................ 351/203; 351/246; 351/239

(58) Field of Classification Search .......... 351/200–246
See application file for complete search history.

(56) References Cited

U.S. PATENT DOCUMENTS 5,051,931 A 9/1991 Chen et al.
5,088,810 A 2/1992 Galanter et al. ............. 351/203

(Continued)

FOREIGN PATENT DOCUMENTS

JP 11-47208 2/1999

(Continued)

OTHER PUBLICATIONS

Zenger et al. 'Isolating Excitatory and Inhibitory Nonlinear Spatial Interactions Involved in Contrast Detection', Vision Res. vol. 36, No. 16, pp. 2497-2513, 1996. December.

(Continued)

*Primary Examiner*—Mohammed Hasan
(74) *Attorney, Agent, or Firm*—Pearl Cohen Zedek Latzer, LLP; Mark S. Cohen

(57) ABSTRACT

The object of the present invention is to provide a system and method to enable a person wishing to improve his vision capabilities to carry with him a training device and to be able to train his vision whenever and wherever he wishes. The current invention makes use of widely available and familiar infrastructure of hand held devices such as cellular phone and cellular network. Other mobile digital devices having visual display may be used, for example: Pocket PC, Palm computer electronic notebook, Personal Digital Assistant (PDA) and even some digital music players such as iPod. Training session comprises of displaying to the trainee sequence of images on the built in display of there hand held device and receiving his response to the displayed images.

26 Claims, 10 Drawing Sheets

U.S. PATENT DOCUMENTS

| | | | | |
|---|---|---|---|---|
| 5,121,981 | A * | 6/1992 | Waltuck et al. | 351/243 |
| 5,308,246 | A | 5/1994 | Belocco | |
| 6,464,356 | B1 | 10/2002 | Sabel et al. | 351/203 |
| 6,876,758 | B1 | 4/2005 | Polat et al. | 382/128 |
| 7,004,912 | B2 | 2/2006 | Polat | 600/558 |
| 7,187,363 | B2 * | 3/2007 | Nguyen et al. | 345/168 |
| 7,346,856 | B2 * | 3/2008 | Nguyen et al. | 715/800 |
| 7,661,821 | B2 * | 2/2010 | Ellenbogen | 351/243 |
| 2003/0109800 | A1 | 6/2003 | Polat | |
| 2003/0232319 | A1 | 12/2003 | Grisham et al. | 351/203 |

FOREIGN PATENT DOCUMENTS

| | | |
|---|---|---|
| JP | 2000-157586 | 6/2000 |
| JP | 2001-54587 | 2/2001 |
| WO | WO 01/47463 | 7/2001 |
| WO | WO 03/092482 | 8/2003 |

OTHER PUBLICATIONS

Adini et al. 'Excitatory-inhibitory network in the visual cortex: psychophysical evidence', Proc. Natl. Acad. Sci. USA, Neurobiology, vol. 94, pp. 10426-10431, Sep. 1997.

Polat U., Sagi D. (1993) Lateral interactions between spatial channels: suppression and facilitation revealed by lateral masking experiments. *Vision Res* ., 33(7), 993-999. Sep. 1993.

Polat U., Sagi D. (1994) The architecture of perceptual interactions. *Vision Res.,* 34(1), 73-78, Sep. 1994.

Polat U., Sagi D. (1994) Spatial interactions in human vision: from near to far via experience-dependent cascades of connections. *Proc. Natl. Acad. Sci. USA,* 91, 1206-1209. Dec. 1994.

Polat U., Norcia A.M. (1996) Neurophysiological evidence for contrast dependent long range facilitation and suppression in the human visual cortex. *Vision Res.,* 36, pp. 2099-2109. Apr. 1996.

Levi D.M., Polat U. (1996) Neural plasticity in adults with amblyopia. *Proc. Natl. Acad. Sci. USA,* 93, pp. 6830-6834. Apr. 1996.

Polat U., Sagi D., Norcia A.M. (1997) Abnormal long-range spatial interactions in amblyopia. *Vision Res.,* 37, pp. 737-744. Sep. 1997.

Levi D.M., Polat U., Hu YS, (1997) Visual improvement in adults with amblyopia. *Invest. Ophthalmol. Vis. Sci.,* 38(8) 1493-1510. May 1997.

Polat U., (1999) Functional architecture of long-range perceptual interactions. *Spatial Vision,* 12, 143-162. Nov. 1999.

Polat, U., Ma-Naim, T., Belkin, M., & Sagi, D. (2004) Improving vision in adult amblyopia by perceptual learning. *Proc Natl Acad Sci U S A,* 101(17): 6692-6697. Jan. 2004.

Bonneh, Y., Sagi, D., Polat, U. (2004) Local and non-local deficits in amblyopia: acuity and spatial interactions. *Vision Res*44(27), 3099-3310.

Tanaka Y. And Sagi D. (1998) Long-lasting, long-range detection facilitation. Vision Research 38. 2591-2599. Mar. 1998.

* cited by examiner 610
620
630

SYSTEMS AND METHODS FOR IMPROVING VISUAL PERCEPTION

CROSS-REFERENCE TO RELATED APPLICATIONS

This application is a National Phase Application of PCT International Application No. PCT/IL2005/000927, International Filing Date Aug. 31, 2005, claiming priority of U.S. Provisional Patent Application 60/607,081, filed Sep. 3, 2004.

FIELD OF THE INVENTION

The invention relates generally to the field of vision improvement and, more specifically, to improving visual perception using cellular phone or a mobile display unit.

BACKGROUND OF THE INVENTION

Human eyesight is a product of two separate processes that work together to form images for a person to "see." One of these processes, herein referred to as the physical component, concerns the physical structure of the various elements of the eye and how incoming light is manipulated and processed by the eye. Defects in the shape of the cornea, the retinal wall, or the optic nerve can impair the functionality of a person's eye and thus impair or eliminate the ability to perceive images. Some of these defects can be corrected through the use of glasses, contact lenses, or surgery.

The second process involved in allowing humans to see images is herein referred to as the neurological component. This component concerns neural processing in the brain and how the brain analyzes information sent from the eyes to produce an image. A person can likewise have a number of defects in this component of the visual process.

The physical component and the neurological component work together to form images that a person sees, or more precisely, that a person perceives. The term "perceives" is preferred because, although the physical component may capture certain details, defects in the neurological component may distort and destroy these details. Alternatively, efficient performance of the neurological component may enhance the image; therefore, the image that is "seen" by the person may not be exactly what the eyes capture. Consequently, the image that is perceived may differ in detail from the image that is seen by the eyes. Thus, the overall process of human eyesight is herein referred to as the visual perception process.

It has been shown that training may improve visual perception of a human subject. These training generally involve displaying images to the trainee.

United States Patent Application 20030109800 to Polat, Uri titled "Systems and methods for improving visual perception" describes a method for improving a common defect in the neurological component of the visual perception process known as amblyopia. This application was published as U.S. Pat. No. 6,876,758 "Methods and systems for improving a user's visual perception over a communications network" to Polat et, al; Apr. 5, 2005; and is incorporated herein by reference.

U.S. Pat. No. 6,464,356 by B. A. Sabel et. al, entitled Process and device for the training of human vision; Oct. 15, 2002; Filed: Apr. 25, 2001, present a process for training the visual system of a human having a zone of intact vision and a zone of deteriorated vision.

Image display apparatus used in the art for training are generally bulky and cannot easily be carried by the trainee.

SUMMARY OF THE INVENTION

Accordingly, it is a principle object of the present invention to provide a system and method to enable a person wishing to improve his vision capabilities to carry with him a training device and to be able to train his vision whenever and wherever he wishes.

The inventive method and system is easy to use and requires little preparation and effort by the trainee.

The method and system according to the current invention uses widely used and familiar infrastructure of hand held devices such as cellular phone and cellular network. Other digital mobile hand held devices having visual display having display area smaller than 250 $cm^2$ may be used. For example: Pocket PC, Palm computer, Electronic Notebook, Personal Digital Assistant (PDA) and even some digital music players such as iPod and portable digital game devices such as "GameBoy" may be used in accordance with the current invention. Such devices may easily be carried by a user and used for vision improvement anywhere, for example while the user is riding a train.

Alternatively, digital mobile hand held device may be replaced by a large screen display device such as a TV, a Laptop computer or Personal Computer (PC) may be used in situations were mobility is not important.

The inventive method can easily be implemented and is suitable for wide spread use.

In an exemplary embodiment of the invention, a system for improving visual perception comprises of a hand held device wirelessly connected to a server computer. The hand held device comprises a display for displaying visual stimuli, means for user input and means for providing feedback to the user.

The hand held device may be a cellular phone, palm computer, PDA, electronic notebook, iPod, portable digital game devices, or alike. The device's integrated display is used for displaying visual stimuli. User response is entered through input means such as keypad of a cellular phone, touch screen of a PDA, key or switches or a microphone.

The visual stimuli may comprise alphanumerical characters. Alternatively, the stimuli may comprise of at least one target structure and at least one flanking structure wherein the target structure in different images has different strength. In another embodiment, visual stimuli may comprise a sequence of images comprising a target image following or followed a masking image.

The method of using the hand held device for visual capability improvement comprises the following steps: (a) registering the user on the server computer, (b) loading the application program on the hand held device and (c) running the application program on the hand held device.

Optionally, at the beginning of each training session, the application program wirelessly contacts the server computer and verifies the authorization for the training session. Optionally, during or at the end each training session, the application program wirelessly contacts the server computer and reports the user score as computed from the number of wrong and correct user responses. Optionally, at the beginning of each training session, the application program wirelessly contacts the server computer and downloads parameters needed to compute the images to be presented to the user.

In one aspect of the invention, a system for training the visual system of a human by presenting visual stimuli to said human is provided comprising: a digital mobile hand held device provided with a display having a display area of no more than 250 cm^2; and a server computer, wherein said server is wirelessly connected to said digital mobile hand held device.

In some embodiments, the system digital mobile hand held device is a cellular phone.

In some embodiments, the digital mobile hand held device is a palm computer.

In some embodiments, usage of the system is billed by the cellular network provider.

In some embodiments, the server communicates with the digital mobile hand held device in order to provide authorization for usage of the system.

In some embodiments, the digital mobile hand held device is held at a distance of less than 50 cm from an eye of the user.

Another aspect of the invention is to provide a method for training the visual system of a human by presenting on a digital mobile hand held device visual stimuli to said human comprising: loading a training program to digital mobile hand held device provided with a display having a display area of no more than 250 cm^2; and executing said training program to display said visual stimuli on said digital mobile hand held device.

In some embodiments, the visual stimuli comprise at least one alphanumerical character.

In some embodiments, the visual stimuli comprise at least one image and wherein the duration of display of said image shortens as the trainee progress.

In some embodiments, the visual stimuli comprise at least two images and wherein the duration of display of at least one of the said images shortens as the trainee progress.

In some embodiments, the visual stimuli comprises at least two images and wherein each image comprises at least one target structure and at least one flanking structure and wherein the strength of at least one of said target structures in at least one of said images is different.

In some embodiments, the visual stimuli comprises at least a first image comprising a target, and a second image similar to said first image for masking said first image, wherein time interval between displaying first and second image is shortened at the trainee progress.

In some embodiments, time interval between displaying first and second image is between 1 second and 0.01 seconds.

In some embodiments, the method for training the visual system of a human according further comprising: identifying visual deficiency of the human; and adopting the visual stimuli based on said visual deficiency.

In some embodiments, said visual deficiency of said human is near-sight.

In some embodiments, said digital mobile hand held device is held at a distance of less than 50 cm from an eye of said human.

Yet another aspect of the invention is to provide a method for training the visual system of a human by presenting visual stimuli to said human comprising: loading a training program to a display device provided with a display having display area larger than 250 cm^2; and executing said training program to display the visual stimuli on said display device, wherein visual stimuli comprises at least a target image comprising a target, and a masking image similar to said first image, wherein time interval between displaying target and masking image is shortened at the trainee progress.

In some embodiments, said time interval between displaying first and second image is between 1 second and 0.01 seconds.

In some embodiments, said display device is positioned at a distance of less than 50 cm from eye of said human.

Further features and advantages of the invention will be apparent from the drawings and the description contained herein.

BRIEF DESCRIPTION OF THE DRAWINGS

An exemplary embodiment of the invention is described in the following section with respect to the drawings. The same reference numbers are used to designate the same or related features on different drawings. The drawings are generally not drawn to scale.

FIG. 2.*b*. shows some details of training session in a method for training the visual system of a human according to an exemplary embodiment of the invention.

DETAILED DESCRIPTION OF EXEMPLARY EMBODIMENT

The following detailed description is of the best presently contemplated modes of carrying out the present invention. This description is not to be taken in a limiting sense, but is made merely for the purpose of illustrating the general principles in accordance with the present invention. The scope of the present invention is best defined by the appended claims.

Digital Mobile Hand Held Display Device.

Figure 1:
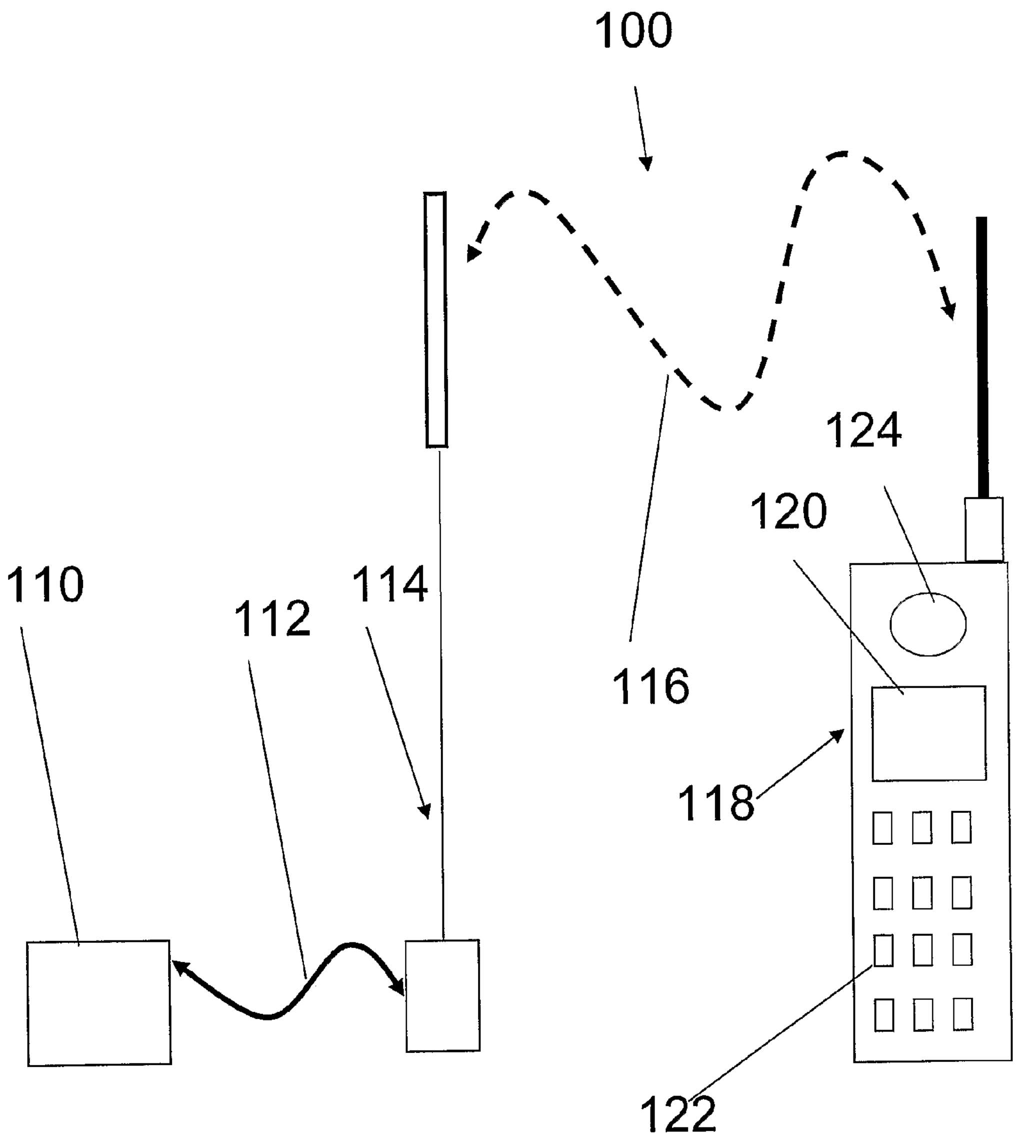
FIG. 1. shows a system for training the visual system of a human by presenting on a hand held display unit visual stimuli to said human according to an exemplary embodiment of the invention.

With reference to the drawings, in FIG. 1 is an illustration of a system 100 for training the visual system of a human by presenting on a digital mobile hand held display unit visual stimuli to said human according to an exemplary embodiment of the invention.

In this exemplary embodiment, the trainee uses a hand held device 118 such as a cellular phone to view visual stimuli. The visual stimuli are generated by a program installed in the hand held device according to parameters stored in the hand held device. Said program controls the hand held device during the training session.

Alternatively, the digital mobile hand held device 118 may be a palm computer, pocket PC, PDA, electronic notebook, iPod player or alike. Specifically, digital mobile hand held device 118 is having display area smaller than 250 $cm^2$. Such devices may easily be held by a user and used for vision improvement anywhere, for example while the user is riding a train.

The hand held display unit device 118 comprises a display 120 and user input means such as keypad 122. In a training session, the trainee is asked to perform a visual task comprising observing the Visual stimulus or a sequence of visual stimuli and respond to it.

The user input may optionally be received by the hand held device using other input means, for example: voice command using the built in microphone in a cellular phone, switches on a mobile "hands free" of headset attachments, touch screen sensor in a pocket PC, palm computer or PDA or other input means which are part of or connected to the hand held device 118.

The hand held device analyzes the user response to determine if the response was correct according to criteria associated with this task.

Criteria associated with this task may comprise reaction time of the user to the stimuli. Long delayed reaction may indicate slow visual processing by the user, while abnormally fast reaction may indicate that the user is guessing without actually perceiving the image.

Optionally, as a response to the user input, the program generates a feedback to be transmitted to the user using plurality of output means.

The output means may be one or few of: audio or visual output means with which the hand held device is equipped. For example, a text or pictorial message may be displayed on the screen 120, a sound or voice message can be generated using a speaker 124. Additionally or alternatively, other output means may be used such as vibration, ring tone or signaling lights whenever available.

Optionally, the feedback provided by the program may comprise encouraging statements such as "good progress" to encourage the trainee to use the application efficiently.

Some accessories may optionally be used with the hand held device. For example, a headset or a hands free attachment could be connected to cellular phone used as the hand held device in accordance to the embodiment of the invention. A head set usually comprises an earphone; a microphone and at least one pushbutton key which may be used as input-output means for receiving user input, for example by the microphone and/or pushbutton, and providing feedback as sound or voice through the earphone. Corded head set or wireless head set, such as "blue tooth" headset may be used. Optionally other accessories such as large screen display may be used.

The distance between the display 120 and the trainee's eye may vary depending on the visual deficiency and the type of training. In some training session the trainee is instructed to hold the hand held device at arm length away. In this situation, the display may occupy approximately ten degrees of the visual field. In contrast to larger displays such as computer screens used in the art, small display used for example in of a cellular phone, when held at distance of approximately 0.5 meter or more, provides training to the central field of view only. However, it is an aspect of the invention to train the central field of vision where visual acuity is most important.

In order to improve near-sight capability, the trainee may be requested to hold the hand held device at shorter distance from his eye, such as 30 or 40 cm. Alternatively, the trainee may be told to position the hand held device at larger distance such as one meter and more. In this case, input/output accessory is preferably used.

The trainee may be requested to remove his glasses or contact lenses for the duration of the session or requested to wear special glasses. Each eye may be trained separately by covering the other eye, or both eyes may be trained as once.

Network Connection to the Server

In one embodiment of the invention the system 100 comprises of a server computer 110.

The server 110 may, from time to time, be connected to the hand held device for example by using Internet and/or phone network to connect to a cellular base station 114 and radio wave to connect to the hand held device.

Alternatively, hand held device 118 may connect locally to another computing device (not shown) which is connected to the server 110. For example, a palm computer may be connected to local PC via cable, IR or RF and the local PC connects to the server using for example a telephone modem, ADSL, LAN or other means. In this way, messages between the server and the hand held device may be exchanged. Messages may be exchanged in this manner even if both connections are not simultaneously active. Various communication protocols may be used to exchange information between the server 110 and hand held device 118. For example, SMS and MMS are widely supported by the cellular networks and allow exchanging short text, data and images. Other, more wideband data exchange protocols exist.

The server, as will be detailed later, may perform various services for the hand held device. For example, the server may hold authorization codes to enable a session by the user holding the hand held device, the server may load the application program to the hand held device, or the server may monitor the training progress of the trainee by receiving and analyzing the user inputs from the hand held device, optionally modifying the program or parameters used to generate visual stimuli.

Optionally, the server is also used to provide billing information according to the utilization of the training application.

Method of Operation

Figure 2A:
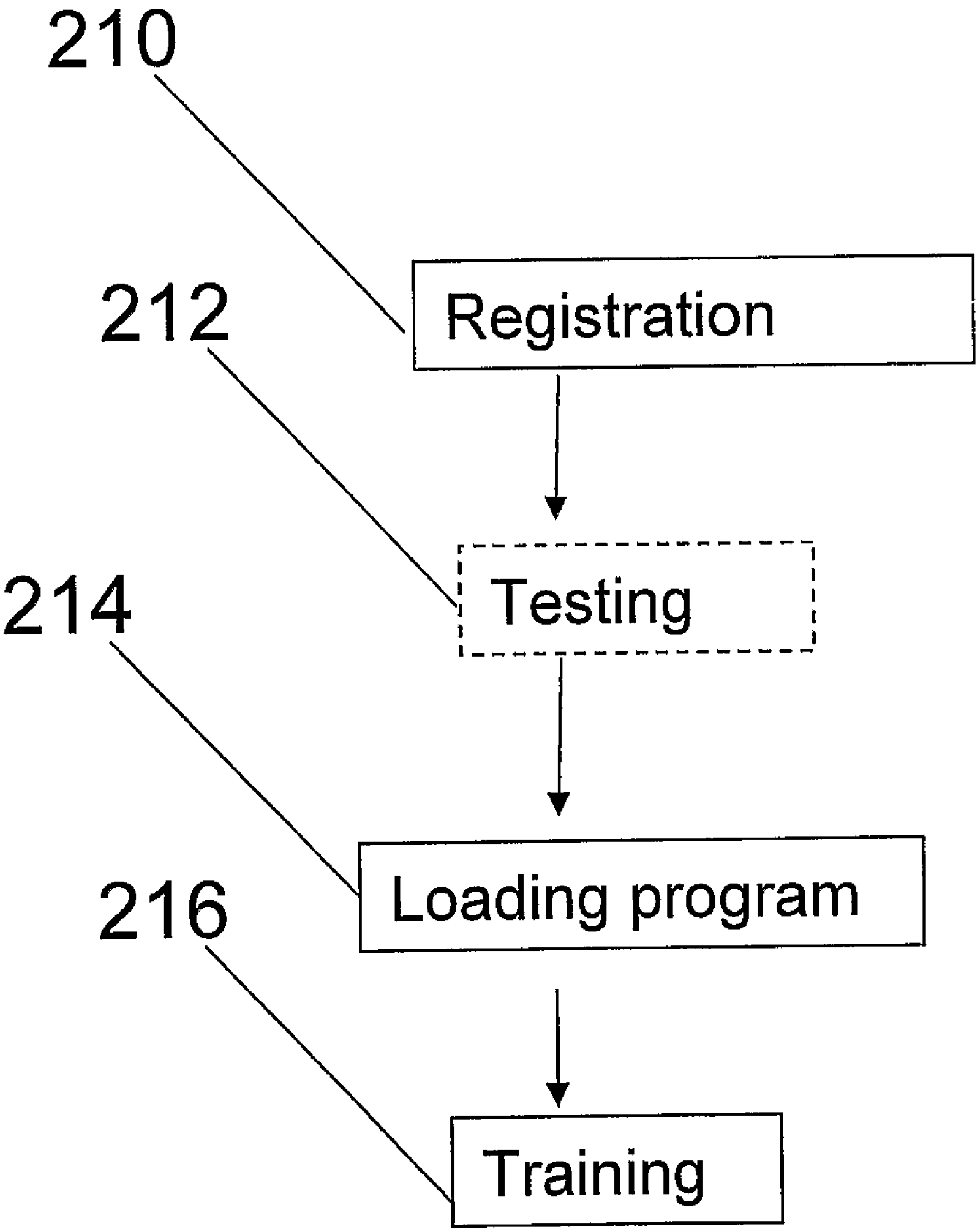
FIG. 2.*a*. depicts a method for training the visual system of a human by presenting on a hand held display unit visual stimuli to said human according to an exemplary embodiment of the invention.
Figure 2B:
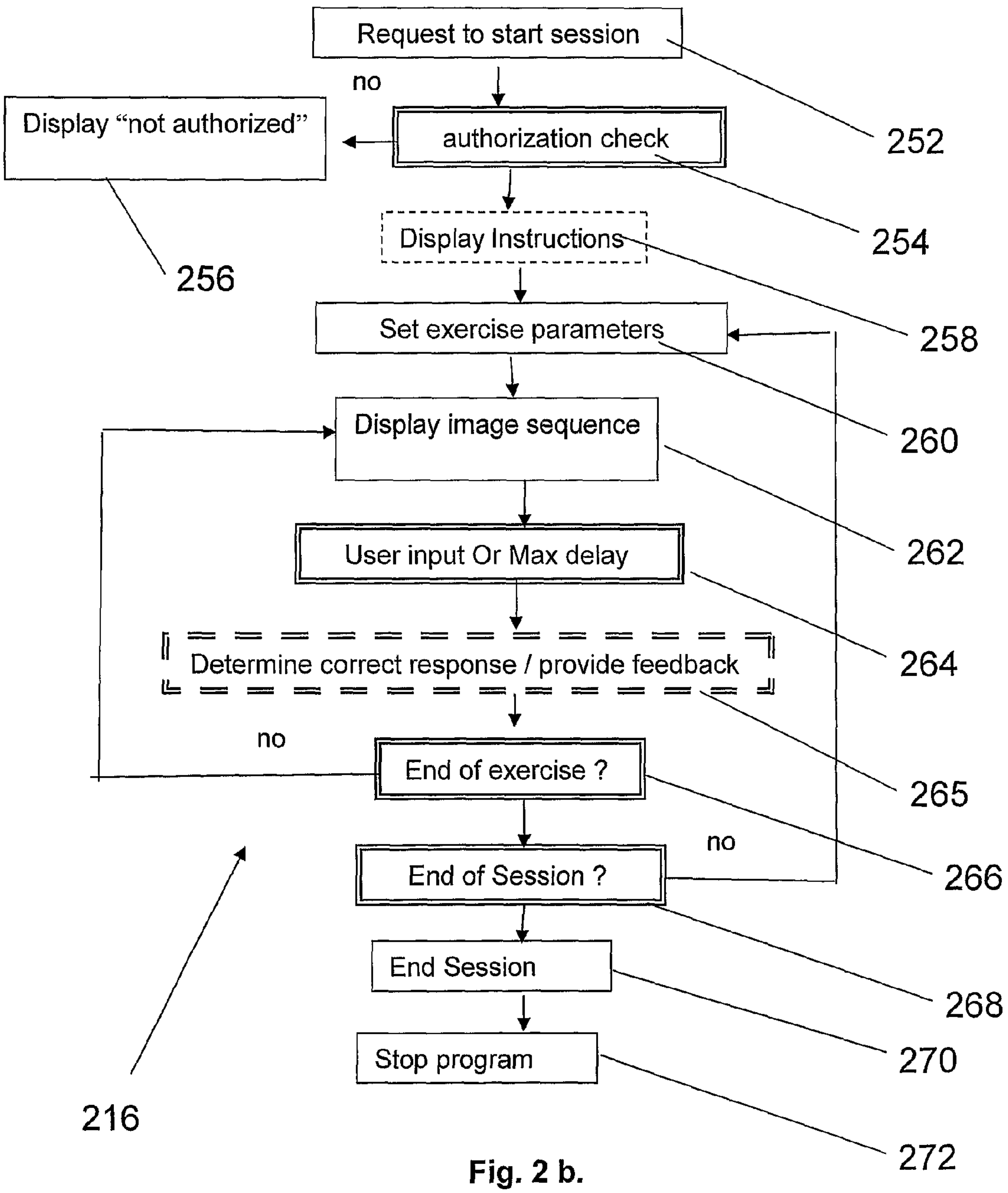

With reference to the drawings, in FIGS. 2*a* and 2*b* are block diagrams of depicting the method according to the current invention. In these drawings, boxes marked by dashed lines represent optional steps and boxes marked by double lines represent steps in which information is tested and a decision is taken. Some optional steps are described in the text but not shown in the drawings.

2*a* is an illustration of a method for training the visual system of a human by presenting on a hand held display unit visual stimuli to said human according to an exemplary embodiment of the invention.

In order to be trained, the trainee must be registered with a provider of the training application.

Optionally, the registration 210 involves visiting the provider office or a clinic where optionally his visual capabilities are tested 212, preferably by a qualified personnel. Testing 210 may be done before or after the registration process, optionally at a different location. Alternatively, a trainee may be referred by his or her doctor or optometrist with a known diagnostics so that further testing is unnecessary.

Alternatively, testing could be done via Internet or using a testing session using the hand held device. This could be done for example during a phone call between the future trainee and the provider using image transfer protocol such as MMS to provide the hand held device with visual stimuli. In some cases, for example when a trainee wants to improve his speed reading abilities, no testing is needed.

After the billing arrangements were made, the training application is loaded 214 to the hand held device.

The method according to the current invention may install an application program in the memory of the hand held device such as a cellular phone. The program may utilize the cellular phone computing power to compute the visual stimuli. Alternately, the stimulation image may be sent from the server 110 on request of the application program using a cellular networking protocol such as SMS or MMS.

Optionally, some of the visual images are generated by the hand held device and other images generated by the server.

In some embodiments of the invention, the application program may run similarly to a cellular phone game.

In one embodiment of the invention, the application program may be loaded to the already existing memory in the cellular phone by a qualified person at distribution location, optionally using appropriate means of interfacing the cellular handset. Alternatively, the application program may be loaded by installing additional memory in existing slot in the handset such as SIMS.

In yet another embodiment, the application program may be loaded by downloading the application wirelessly using the cellular networking protocol.

In this case, the application may be loaded once and used for several sessions or alternatively, the application may be downloaded before each training session.

After the application loading 214 is complete, the trainee may start training session 216.

The steps involve in using other types of hand held device, such as Palm PC, iPod, portable digital game or PDA are similar. Methods of loading program 214 in this case may involve using cable or wireless communication means such as LAN, USB, Infra-Red (IR), Bluetooth, RF-LAN, etc.

Training Session

FIG. 2.*b*. shows some details of training session in a method for training the visual system of a human according to an exemplary embodiment of the invention.

A training session 216 starts when a trainee request a training session 252 by a accessing the application program installed in the hand held device.

The application program performs an authorization check 254 to verify if the user has the right to a training session. This can be done locally within the hand held device or by requesting an authorization from the server 110.

One or combination of few authorization methods may be used: The user may be requested to input a password, the ID of the hand held such as the phone number of a cellular phone may be verified by the server, timely payment or other billing information may be checked by the server, the number of session already exhorted used may be compared to the number of session paid for. Alternatively or additionally, or consistency of past session performance may be analyzed to determine if few different users are sharing the application.

If authorization is not granted, the application may display a warning message such as "session not authorized" message 256, and training session would not start.

If authorization is granted, the application optionally displays instructions 258 for the coming session. An experience trainee may skip the instruction.

Each training session comprises a plurality of exercises. To start an exercise, the application set the exercise parameters 260. Optionally, exercise parameters 260 are preset for all training sessions during loading of the program. Alternatively, computing the exercise parameters may be done on server 110 and be transmitted to the hand held device, or the parameters may be computed by the application in the hand held device.

Optionally, trainee's progress is used to compute the parameters. Optionally a qualified person at remote location view from time to time the progress made by the trainee and adjusts the parameters accordingly. In this case, trainee progress is optionally accessed assessed by the qualified person optionally using the Internet.

The parameters define the type of image to be used as visual stimuli, its size, its contrast, sequence of stimuli, the duration of display of each stimulus the delay between images etc. The parameters also define for each visual task what is the correct user response 264 and what is the time interval within which the response should be given 264. Optionally, the parameters also define a maximum time interval after which the task is skipped or the session paused or ends if the user does not respond.

Optionally, the program analyzes the trainee's response and gives it a score based on the type of the response and optionally based on the time of the response.

Optionally a feedback 265 is displayed to the trainee after the visual task. Alternatively, an average score or feedback or both are displayed at the end of an exercise 266 or at the end of a session 270. Generally, parameters for the full Exercise are pre-calculated. The parameters of an image do not necessarily depend on the user response to the preceding task.

Visual Task

In a visual task, the trainee is presented with a visual stimulus or an image sequence 262 and the trainee is requested to observe the image or images and provide a response.

For example, in a visual task the trainee is required to locate a visual target in an image and respond with yes/no if a target was located in an image or not.

Alternatively, a sequence of images my be displayed and the trainee has to identify—when the target appeared or which of the images in the sequence include a target.

Figure 3:
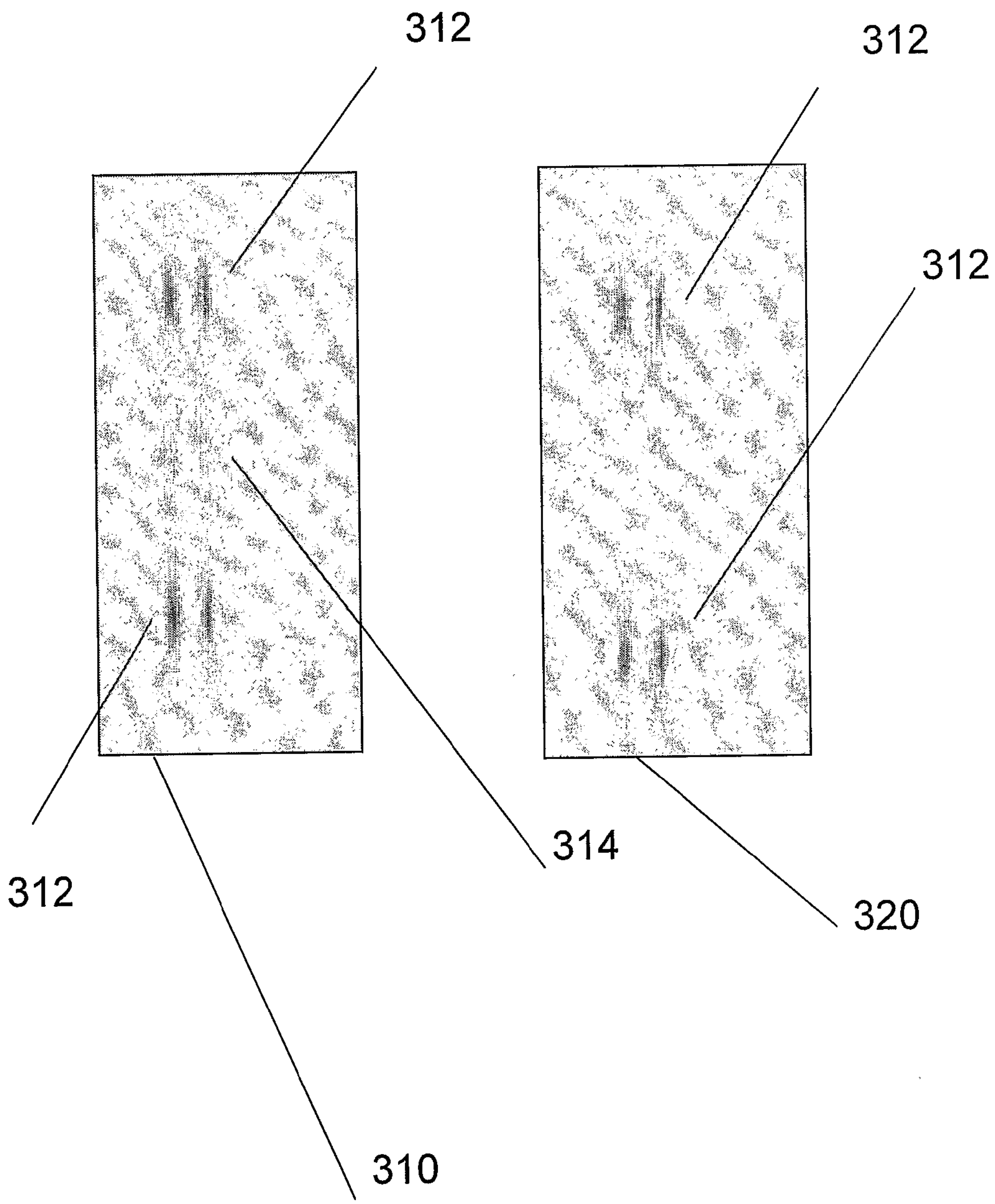
FIG. 3. is an illustration of an embodiment of a visual stimulus for training the visual system of a human as known in the art.

FIG. 3. shows such a sequence as known in the art. The exemplary sequence consists of two images: first image 310 including target structure 314 and flanking structures 312; and second image 320 including only flanking structures 312. A correct response in this example will be for example pressing the key #1 to identify that the target was in the first image.

Figure 4A:
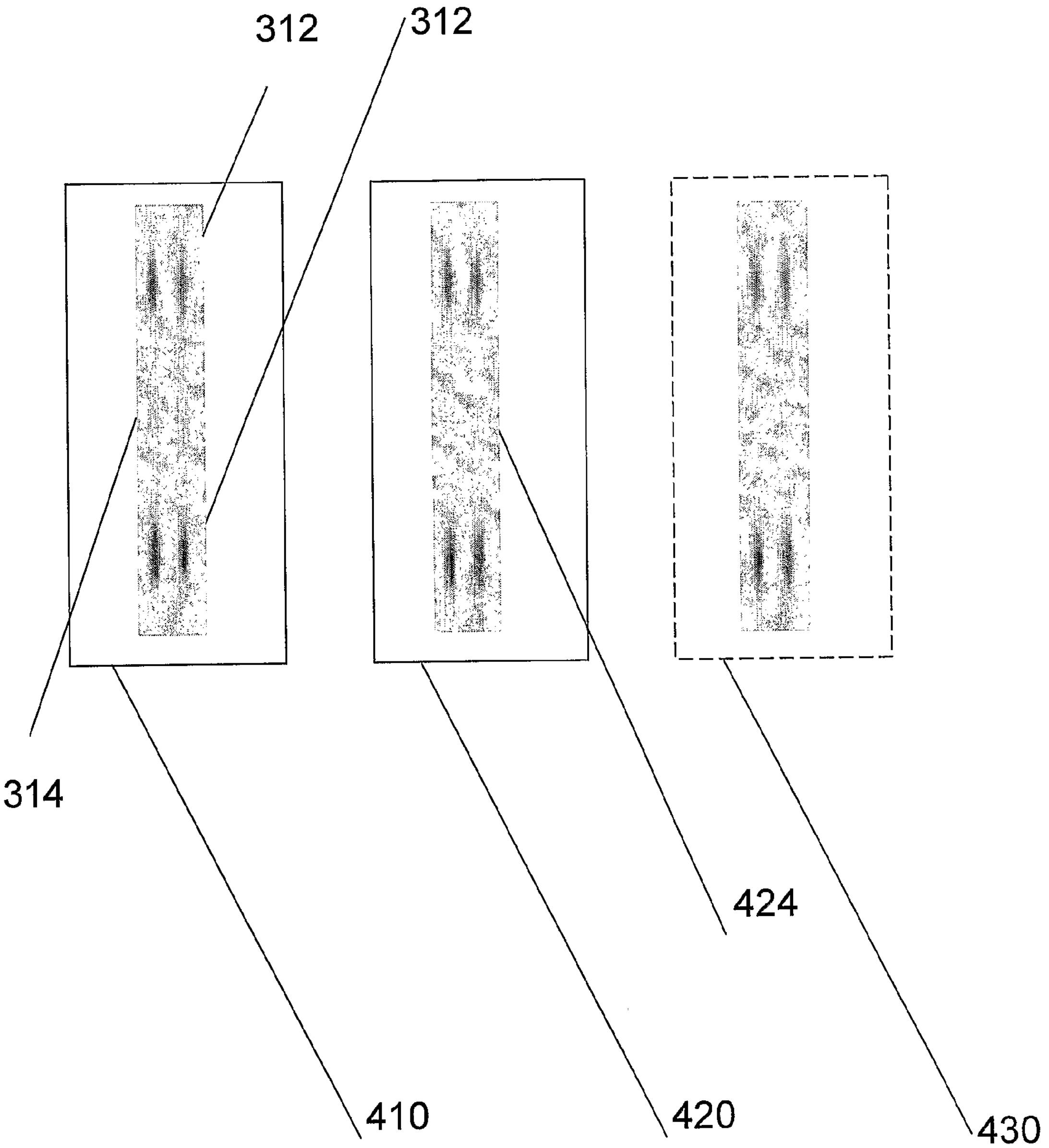
FIG. 4.*a*-to 4.*c* are illustrations of an embodiment of a visual stimuli for training the visual system of a human according to some exemplary embodiments of the invention.
Figure 4B:
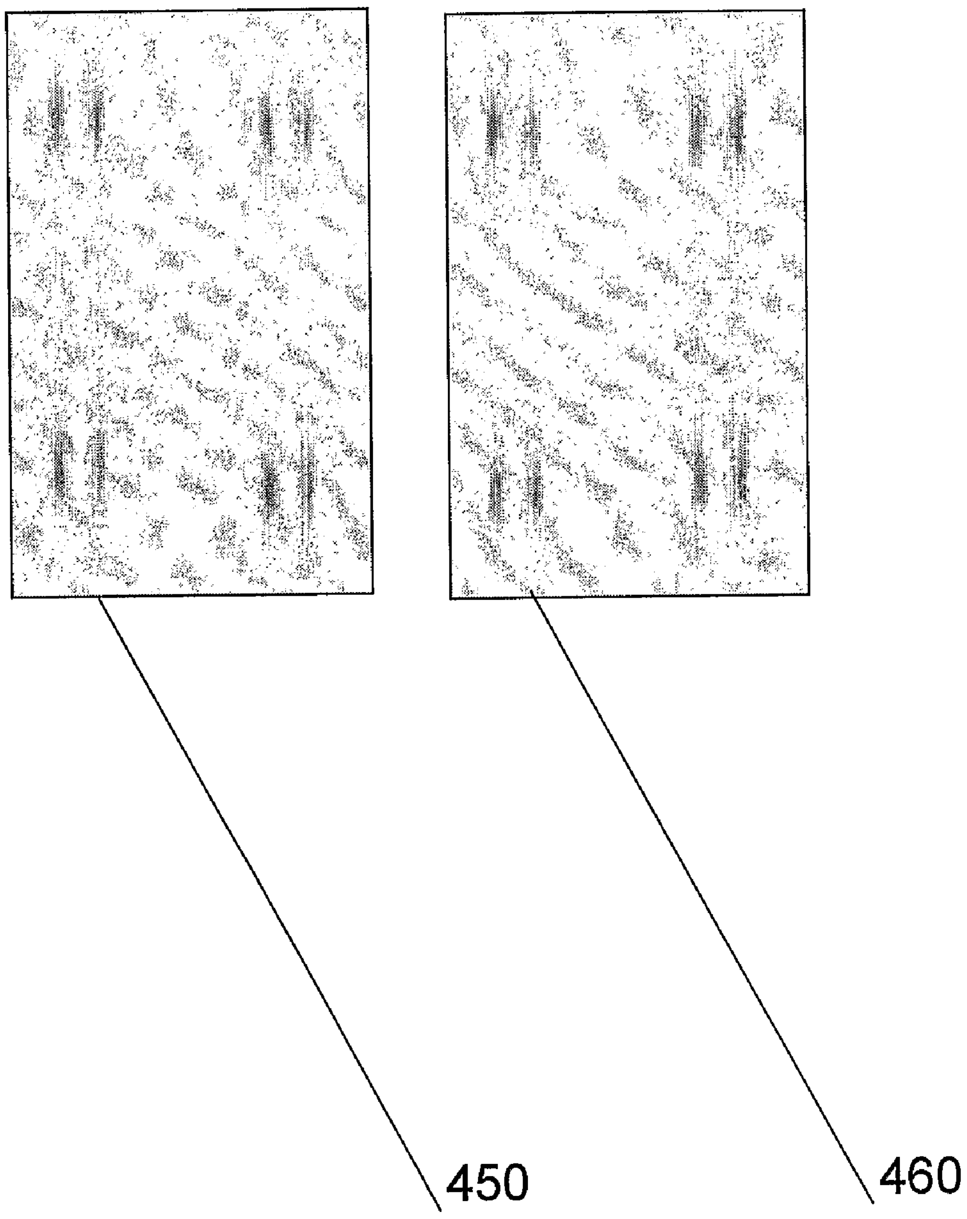
Figure 4C:
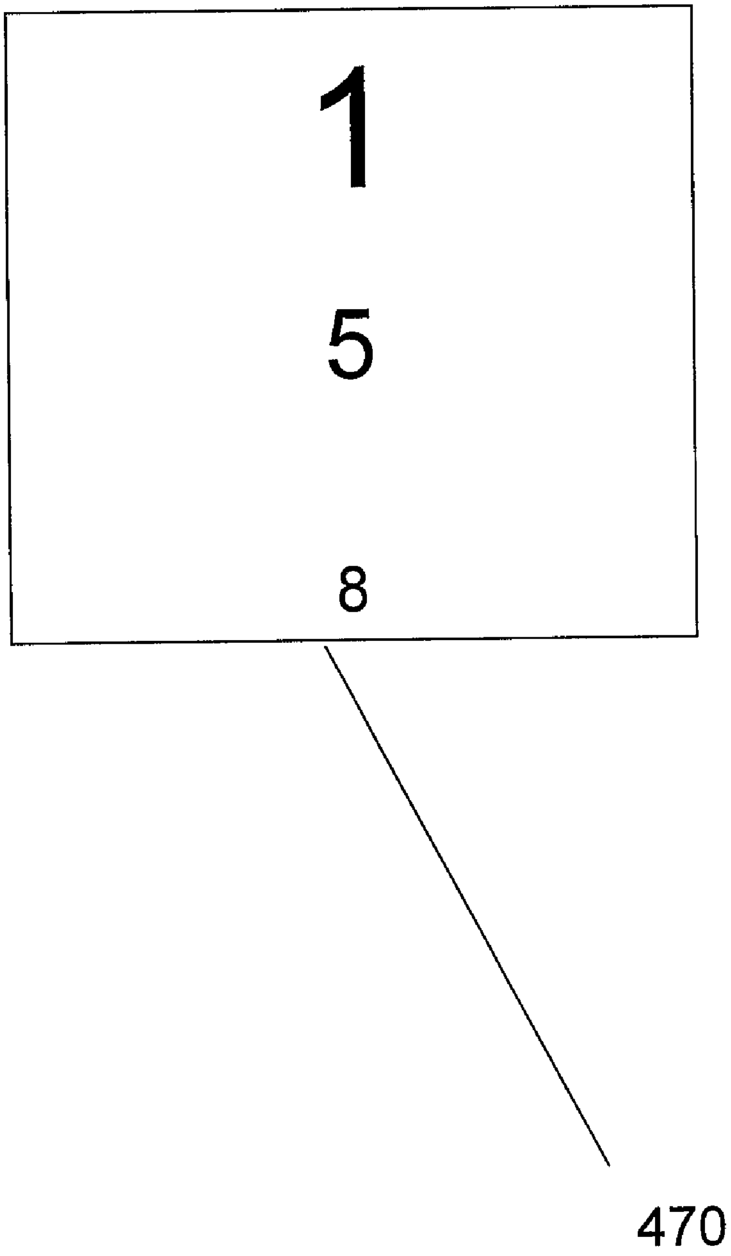

In contrast, FIG. 4.*a*. shows a sequence of at least two images 410, and 420 each comprises plurality of flanking structure 312 and at least one target structure, but the target structures 314 and 424 are of different strength. Strength of a target may be its size, contrast, difference in shade or color, etc.

Alternatively a sequence of more than two images such as 410, 420 and 430; may be shown, optionally in cyclic manner and the proper user response would be to respond when the target with the highest strength is presented. Alternatively, the visual task may be to identify the absence of a target in one of a sequence of images. Alternatively, flanking structures may be missing and the visual task is to identify a change in the target's strength.

Alternatively, the visual task may be to count the number of images in a sequence. For example, a collection of images, some identical, similar or distinct images may be presented in rapid sequence to the trainee, and his task is to identify the number of images in the sequence, the number or different or identical images in the sequence, etc. Alternatively, or additionally, the visual task may be to identify changes of the presented images.

Similarly, the trainee may be requested to respond by identifying the location of a target within the image such as left/right/up/down. An example for such a task can be seen in FIG. 4.*b*. where two images are seen: First image 450 in which the target is located on the left and second imager 460 wherein the target location is on the right.

In another embodiment of the invention, at least two images are presented, at least one of these imagers is displayed for a different duration.

For example, first image may be displayed for a duration of 100 milliseconds and second image for a duration of 130 milliseconds. The visual task is to identify the image displayed for longer (or shorter time). It is clear to realize that the task is easy when the times are long and the differences are large.

A training program may start with such easy tasks and progress to more difficult settings.

Numerous combinations of such visual tasks may be created by a person skilled in the art.

In FIG. 4.*c*. an image 470 in which digits of varying sizes are presented.

Similarly images containing words with of varying length may be presented to the trainee for short duration in order to develop fast reading capabilities. The trainee is than required for example to identify if the image contains a legal word.

Other tasks could be designed for example; an image with slowly increasing target strength wherein the task is to press a key as soon as the location of the target is determined or as soon as the target is observed.

The task is scored according to the parameters for being the correct response and optionally by the time taken by the trainee to respond.

In another type of visual tasks may be aimed at increasing the speed of visual image processing by the trainee. A sequence of images is shown in with decreasing delay between them.

The sequence of images may comprise a target image following a masking image. The duration of target image display decreases as the trainee improves his score. The target image may be a digit, a number, a letter or a word or an identifiable image.

Current researches by the inventor and his colleagues have indicated that training may increase the speed in which images are processed.

Figure 5:
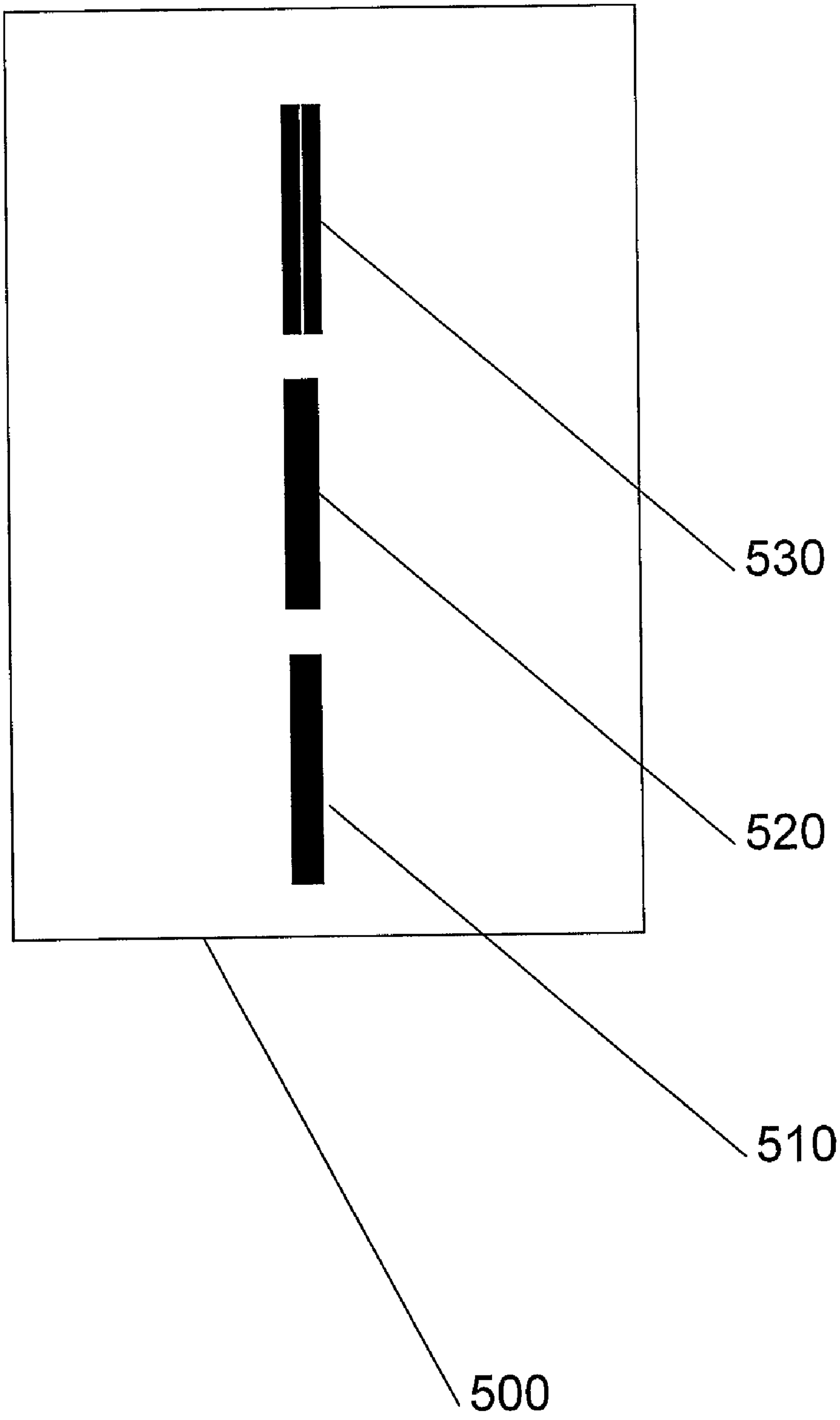
FIG. 5. is an illustration of an embodiment of a visual stimuli for training the visual system of a human according to some exemplary embodiments of the invention.

FIG. 5. is an illustration of an embodiment of a visual stimuli for training the visual system of a human aimed to improve visual resolution. The image 500 includes at least one pair of lines separated by a narrow gap. In the example of FIG. 5, three such pairs are shown: zero gap 510, narrow gap 520 and wide gap 530.

In the preferred embodiment, a target image is displayed for a short time followed by a masking image which is similar to the target image but with at least one difference. For example image 310 and 320 may be used as target and masking images. Alternatively, masking image is dissimilar, optionally random noise.

Figures 6A, 6B, 6C:
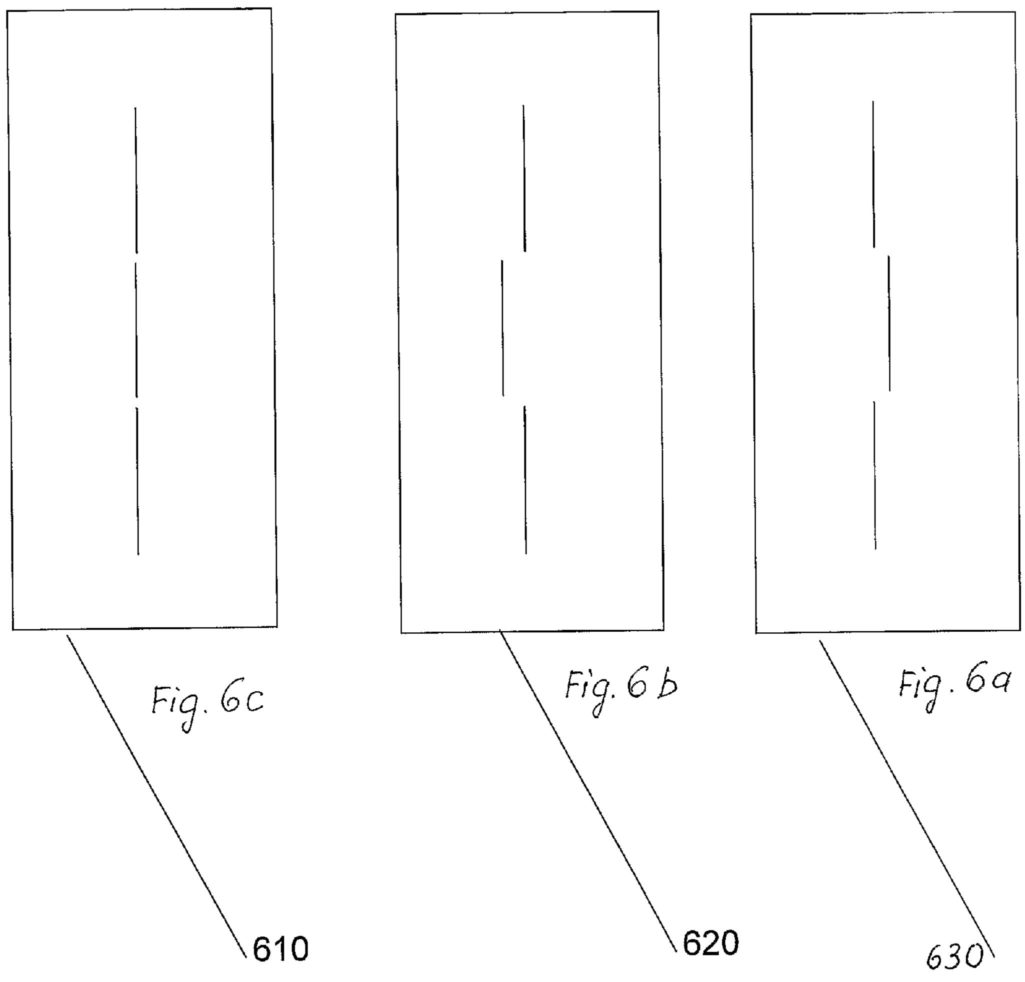
FIG. 6.*a*. to 6.*c*. are illustrations of an embodiment of a visual stimuli for training the visual system of a human according to some exemplary embodiments of the invention.
Figure 7:
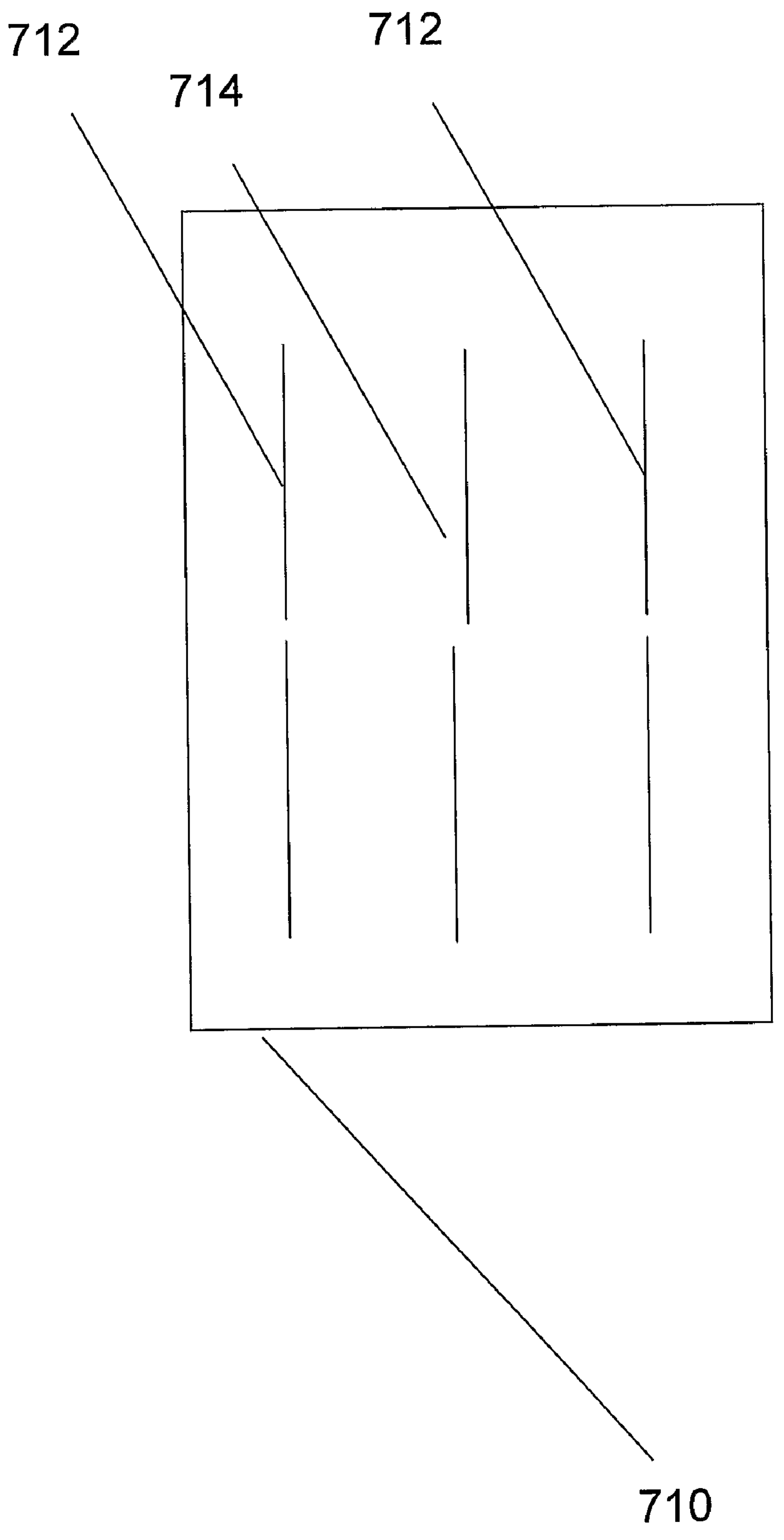
FIG. 7. is an illustration of an embodiment of a visual stimuli for training the visual system of a human according to some exemplary embodiments of the invention.

Preferably, the two images are shown at the same or close place in the visual field. The training starts with long time separation between the two images, for example 0.3 to 1 second. As the trainee gain speed, the time interval is shortened. At some short time interval the person no longer able to identify the target due to the masking effect of the second image. In a normal person this time interval is approximately 180 milliseconds. Longer times were observed in dyslectic patients. Experiments have shown that this time may be shortened to 30 milliseconds. Since in everyday life, the human's visual system is "bombarded" with visual signals, the processing speed of the brain is one of the limiting factors to visual perception, and improving it may improve vision without actually changing the optical components of the vision. Similarly, condition of dyslectic patients may improve by this type of training. The lines, gap and background of structures, for example as seen in FIGS. 5, 6 and 7 may be in different colors and contrast. The lines may be at various length and orientation.

In the example of FIG. 5, trainee is requested to identify the narrow gap.

FIG. 6.*a*. to 6.*c*. are another illustrations of an embodiment of a visual stimuli. In this example, the trainee is requested to identify in what direction the central section of the line is displaced: to the right as in image 630, to the left as in image 620 or not at all as in image 610.

FIG. 7. is another illustrations of an embodiment of a visual stimuli. In this example, the image 710 comprises a target structure 714 and two flanking structures 712. The trainee is requested to identify if the top section of the target structure 714 is displaced and if so—in what direction.

Feedback.

Feedback informing the trainee about the degree of his success may be given immediately after the response 265 or as average score at the end of each exercise 266 or at the end of a session 270 or in a combination of few of these methods.

At the end of each exercise, the application determines if the session has reached its end 268. If so, the application is closing the session 270 by optionally providing the trainee a feedback about its progress during the session and optionally transmitting information to the server 110 regarding the session. The application then stops 272.

Optionally, the server receives information at end of each or some of the s or at the end of each or some of the sessions or exercise. Exercise may be scored according to the individual progress of the trainee as judged by his recorded history of his response, optionally compared to average progress by trainee with similar condition.

If during a session, the training is interrupted, for example when the hand held device is a cellular phone and the cellular phone receives an incoming call, the application may be configured to pause for the duration of the call and resume when the call ends. Alternatively, the application may stop on interruption or pause for a maximum duration than stop. The ringer or vibrate mode of a cellular phone may be configured to be active or inactive to allow or prevent interruption by incoming call during the training session.

Optionally, the application may be configured to re-start a task or restart the exercise or restart the session after interruption. If the application is stopped in mid-session, it may be configured to start where it stopped or to re-start the session.

Optionally, a set of exercises may be prepared, each defined by its parameters. Preferably, the exercises are arranged in increasing level of difficulty. The trainee may optionally start a more difficult exercise only if he reached a minimal score in the preceding exercise.

Billing and Means to Avoid Abuse by Unauthorized User.

Several modes of payment can be applicable for the method according to the current invention:

A fixed price could be charged when the application program is installed. This payment may enable the trainee to use the application for a set calendar duration optionally only for a set number of session per day. Alternatively a total of a set number of session are enabled or until a preset progress was made.

Alternatively, a "per-use" fee can be charged, initiated by server 110 whenever a session is requested. Alternatively, "Air-time" fee charged by the cellular network for communication between server 110 and hand held device 118 could be shared with the application provider.

Methods for preventing unauthorized copy or use of computer programs such as hardware key or a password-generating device may be used to protect the application.

While the invention has been described with reference to certain exemplary embodiments, various modifications will be readily apparent to and may be readily accomplished by persons skilled in the art without departing from the spirit and scope of the above teachings.

It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe the best mode contemplated by the inventors and therefore include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims. The terms "comprise", "include" and their conjugates as used herein mean "include but are not necessarily limited to"

The invention claimed is:

1. A method for training a visual system in a human user comprising the steps of:

(a) presenting to said user a sequence of consecutive images comprising: (1) at least a first consecutive image and a second consecutive image; and (2) at least one target structure or at least one target image;

(b) receiving a feedback from said user indicating whether said user has identified said at least one target structure or at least one target image; and (c) shortening the time interval between the presentation of said first consecutive image and said second consecutive image as said vision improves in said user.

2. The method of claim 1, wherein said training is improving.

3. The method of claim 1, further comprising the step of presenting to said user at least one consecutive image for a shorter period or a longer period compared to the presentation period of the remaining consecutive images in said sequence.

4. The method of claim 1, wherein said sequence of consecutive images comprises at least one target image and at least one masking image.

5. The method of claim 4, wherein the strength of said target image and said masking image differ.

6. The method of claim 1, wherein said sequence of consecutive images comprises at least one target structure and at least one flanking structure.

7. The method of claim 6, wherein the strength of said target structure and said flanking structure differ.

8. The method of claim 1, wherein said at least a first consecutive image and a second consecutive image comprise at least one alphanumerical character.

9. The method of claim 1, wherein said presenting is in a single field of view.

10. The method of claim 1, wherein said sequence is presented on a screen of a portable device.

11. A device for training a performance of a visual system in a human user comprising:

(a) a computing unit; and (b) a display presenting a sequence of consecutive images generated by said computing unit, said sequence of consecutive images comprises: (1) at least a first consecutive image and a second consecutive image; and (2) at least one target structure or at least one target image; wherein said computing unit shortens the time interval between the presentation of said first consecutive image and said second consecutive image as said performance of said visual system in said user improves.

12. The device of claim 11, wherein said training is improving.

13. The device of claim 11, wherein said computing unit further shortens or prolongs the presentation period of at least one consecutive image compared to the presentation period of the remaining consecutive images in said sequence.

14. The device of claim 11, wherein said sequence of consecutive images comprises at least one target image and at least one masking image.

15. The device of claim 14, wherein the strength of said target image and said masking image differ.

16. The device of claim 11, wherein said sequence of consecutive images comprises at least one target structure and at least one flanking structure.

17. The device of claim 16, wherein the strength of said target structure and said flanking structure differ.

18. The device of claim 11, wherein said presenting is in a single field of view.

19. The device of claim 11, wherein said device is a portable device.

20. The device of claim 11, further comprising an input means to enable said user to signal of identification of said target image or said target structure in said sequence of consecutive images.

21. A system for training a visual system in a human user comprising:

(a) a computing unit; and (b) a display presenting a sequence of consecutive images generated by said computing unit, said sequence of consecutive images comprises: (1) at least a first consecutive image and a second consecutive image; and (2) at least one target structure or at least one target image; wherein said computing unit shortens the time interval between the presentation of said first consecutive image and said second consecutive image as said performance of said visual system in said user improves.

22. The system of claim 21, further comprising an input means to enable said user to signal of identification of said target image or said target structure in said sequence of consecutive images.

23. The system of claim 21, further comprising a server linked to said device.

24. The system of claim 23, wherein said server performs at least one operation selected from the list consisting: authorizing said user, downloading a training program to said device, monitoring a training progress of said user, generating a sequence of consecutive images comprising: (1) at least a first consecutive image and a second consecutive image; and (2) at least one target structure or at least one target image, or modifying parameters used to generate said image or said structure.

25. The system of claim 23, wherein said server comprises said computing unit.

26. The system of claim 21, wherein said training is improving.

* * * * *